United States Patent
Dahdouh

(10) Patent No.: US 11,497,564 B2
(45) Date of Patent: Nov. 15, 2022

(54) SUPERVISED ROBOT-HUMAN COLLABORATION IN SURGICAL ROBOTICS

(71) Applicant: Verb Surgical Inc., Mountain View, CA (US)

(72) Inventor: Andrew Dahdouh, Campbell, CA (US)

(73) Assignee: Verb Surgical Inc., Mountain View, CA (US)

( * ) Notice: Subject to any disclaimer, the term of this patent is extended or adjusted under 35 U.S.C. 154(b) by 438 days.

(21) Appl. No.: 16/434,892

(22) Filed: Jun. 7, 2019

(65) Prior Publication Data
US 2020/0383734 A1 Dec. 10, 2020

(51) Int. Cl.
| | |
|---|---|
| B25J 9/16 | (2006.01) |
| A61B 34/00 | (2016.01) |
| A61B 34/32 | (2016.01) |
| A61B 34/35 | (2016.01) |
| A61B 17/00 | (2006.01) |

(52) U.S. Cl.
CPC .............. *A61B 34/25* (2016.02); *A61B 34/32* (2016.02); *A61B 34/35* (2016.02); *A61B 34/76* (2016.02); *A61B 2017/00477* (2013.01); *A61B 2034/252* (2016.02); *A61B 2034/258* (2016.02); *B25J 9/1689* (2013.01); *G05B 2219/40* (2013.01)

(58) Field of Classification Search
USPC ................................................. 700/245–264
See application file for complete search history.

(56) References Cited

U.S. PATENT DOCUMENTS

| | | | | |
|---|---|---|---|---|
| 6,099,522 A | * | 8/2000 | Knopp | A61F 9/00804 606/5 |
| 7,831,292 B2 | * | 11/2010 | Quaid | A61B 34/37 345/157 |
| 8,868,241 B2 | * | 10/2014 | Hart | B25J 9/1661 700/264 |
| 9,272,418 B1 | * | 3/2016 | Guerin | B25J 9/1661 |
| 9,788,903 B2 | * | 10/2017 | Kim | A61B 34/30 |

(Continued)

OTHER PUBLICATIONS

International Search Report and the Written Opinion for International Patent Application PCT/US2019/036247 dated Apr. 7, 2020.

(Continued)

*Primary Examiner* — Jonathan L Sample
(74) *Attorney, Agent, or Firm* — Lempia Summerfield Katz LLC

(57) ABSTRACT

A surgical robotic system offers automation templates, such as surgical task templates, for collaborative control of the robot arms operating in an automated manner. This automated operation through integration of template selection and programming may reduce fatigue while maintaining accuracy and dexterity. For more routine parts of the surgery, the surgeon may select a template and use the template interface to set various parameters for a given surgery, such as the force to be applied, order of tasks, trajectory of movement, stop points, and/or distance of any given movement in automatic operation for surgeon verification. By automating parts of the surgery, the surgeon may use direct control for more sensitive aspects of the surgery while having a respite or assistance for more routine aspects of the surgery.

19 Claims, 4 Drawing Sheets

(56) References Cited

U.S. PATENT DOCUMENTS

| | | | |
|---|---|---|---|
| 10,537,399 B2* | 1/2020 | Eckert | A61B 34/76 |
| 2010/0174410 A1* | 7/2010 | Greer | A61B 34/37 700/264 |
| 2011/0015637 A1* | 1/2011 | De Smedt | A61B 17/175 606/89 |
| 2012/0053597 A1* | 3/2012 | Anvari | A61B 34/35 606/130 |
| 2014/0005684 A1* | 1/2014 | Kim | G16H 20/40 606/130 |
| 2014/0142422 A1* | 5/2014 | Manzke | A61B 5/4839 600/424 |
| 2014/0222023 A1* | 8/2014 | Kim | A61B 34/30 606/130 |
| 2014/0378995 A1* | 12/2014 | Kumar | A61B 5/065 606/130 |
| 2016/0058517 A1* | 3/2016 | Kim | A61B 34/30 606/130 |
| 2016/0199141 A1* | 7/2016 | Mewes | A61B 34/30 700/253 |
| 2016/0331474 A1* | 11/2016 | Lacal | A61B 34/35 |
| 2017/0258538 A1* | 9/2017 | Cohen | A61B 17/28 |
| 2018/0250086 A1* | 9/2018 | Grubbs | A61B 34/35 |
| 2019/0015167 A1* | 1/2019 | Draelos | A61B 34/76 |
| 2020/0289222 A1* | 9/2020 | Denlinger | B25J 9/1694 |

OTHER PUBLICATIONS

Daluja S. et al., An integrated movement capture and control platform applied towards autonomous movements of surgical robots, Stud Health Technol Inform. 2009; 142:62-7; 2 pp.

Eliza Strickland, Autonomous Robot Surgeon Bests Humans in World First, Science Translational Medicine; May 4, 2016; 3 pp.

John Schulman et al., A Case Study of Trajectory Transfer Through Non-Rigid Registration for a Simplified Suturing Scenario, 2013 IEEE/RSJ International Conference on Intelligent Robots and Systems; 7 pp.

Joshua James et al., Prophetic Goal-Space Planning for Human-in-the-Loop Mobile Manipulation, 2015 IEEE-RAS 15th International Conference on Humanoid Robots (Humanoids); 8 pp.

Michael Yip et al., Robot Autonomy for Surgery, World Scientific Review Volume; Jul. 12, 2017; 33 pp.

Pierre Berthet-Rayne et al., A three state Human-Robot collaborative framework for bimanual surgical tasks based on learned models, 2016 IEEE International Conference on Robotics and Automation (ICRA); 9pp.

Procedings of the Performance Metrics for Intelligent Systems Workshop, Aug. 28-30, 2007; 189 pp.

Stephen Hart et al., Affordance Templates for Shared Robot Control, AAAI Fall Symposia 2014; 2 pp.

Stephen Hart et al., The Affordance Template ROS Package for Robot Task Programming, 2015 IEEE International Conference on Robotics and Automation (ICRA); 8 pp.

* cited by examiner

SUPERVISED ROBOT-HUMAN COLLABORATION IN SURGICAL ROBOTICS

BACKGROUND

The present embodiments relate to operation of a surgical robot. Minimally-invasive surgery (MIS) may be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. One existing robotically-assisted surgical system has a surgeon console that resides in the same operating room as the patient and a patient-side cart with four interactive robotic arms controlled from the console. Three of the arms hold instruments such as scalpels, scissors, or graspers, while the fourth arm supports an endoscope camera. Using the robotic system, the surgeon directly controls the robotic arms during MIS. This direct control of the robotic arms provides for motion accuracy, dexterity, and allows for presentation of information on a user interface not normally available to the surgeon. However, the surgeon may suffer from physical and/or mental fatigue during the surgery even using the robotic system. Controlling of each motion of the robotic arms, like controlling one's hands, over an entire surgery may result in loss of accuracy and dexterity.

SUMMARY

By way of introduction, the preferred embodiments described below include methods, systems, instructions, and computer readable media for use of robotic systems to reduce fatigue, maintaining accuracy and dexterity. The robotic system offers automation templates, such as surgical task templates, for collaborative control of the robot arms operating in an automated manner. This automated operation through integration of template selection and programming may reduce fatigue while maintaining accuracy and dexterity. For more routine parts of the surgery, the surgeon may select a template and use the template interface to set various parameters for a given surgery, such as the force to be applied, order of tasks, trajectory of movement, stop points, and/or distance of any given movement in automatic operation for surgeon verification. By automating parts of the surgery, the surgeon may use direct control for more sensitive aspects of the surgery while having a respite or assistance for more routine aspects of the surgery.

In a first aspect, a surgical robotic system includes one or more robotic arms and one or more surgical tools each coupled to a distal end of the respective one or more robotic arms. A memory is configured to store a plurality of task templates. Each of the task templates includes a sequence of steps for automated performance of a surgical task by the surgical tools and including one or more parameters controlling one or more of the steps of the respective task template. A user interface is configured for user selection of one of the task templates and settings for the one or more parameters for the selected task template. The one or more parameters for the selected task template include: a trajectory of arm and/or tool movement, a force level for tissue manipulation, a stop point for user verification, and/or an order of the steps in the sequence. A processor is configured to automatically drive the robotic arms and the robotic surgical tools based on the selected task template and the settings.

In a second aspect, a method is provided for surgery by a surgical robot. A user in teleoperation places a surgical instrument relative to a surgical site using a robot arm in surgery of a patient. A surgical template is selected from a menu. A value of a parameter of the selected surgical template is selected. The surgical robot automatically performs a surgical task following the selected surgical template based on the value of the parameter. The automatic performance includes movement of the robot arm and surgical instrument without the movement being controlled by the user during the movement.

In a third aspect, a non-transitory computer readable storage medium has stored therein data representing instructions executable by a programmed processor for automated robot surgery by a surgical robot. The storage medium includes instructions for setting values for parameters of a surgical task template for surgery by the surgical robot, and automatically operating the surgical robot in surgery according to the surgical task template with the set values.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Task-centric control in robotics is an intuitive approach to leveraging robotics technology in a user friendly and highly decoupled manner. The leveraging of affordance or other task templates as a computational construct allows for surgeons to utilize robotic manipulators to enact various tasks through a supervised human-in-the-loop autonomous setting for improved surgical workflow from a user standpoint as well as efficiency in critical procedures. Leveraging affordance or other task templates for surgical robots allows for better surgical workflow as well as success in surgery for democratizing surgery.

Templates may be applied to various surgical tasks, such as surgical tasks for a third arm (e.g., the surgeon directly controls two arms while the motion of the third arm is automated using the surgical task template). Common tasks, such as utilizing the tertiary manipulator and tool to retract organs in the workspace of the procedure or other simple tasks, may be automated.

Surgical robots improve surgical success through improvement of motion accuracy, dexterity, and presentation of information in meaningful ways. By automating operation of one or more robot arms in surgery, the accuracy, reproducibility, fatigue, and/or safety may be improved. Low level automation allows the surgeon to focus on the most difficult aspects of a surgical procedure, leaving tedious tasks to the robotic system.

Various robotic surgical systems may be used with task templates, such as surgical task templates, for automation of surgical tasks. A robotic surgical system, surgical robot, or robotic-assisted surgical system is a software-controlled, electromechanical system designed for surgeons to perform MIS or other types of surgery. The surgical robotic system can be used with an endoscope, compatible endoscopic instruments, and/or accessories. The system may be used by trained physicians in an operating room environment to assist in the accurate control of compatible endoscopic instruments during robotically-assisted urologic, gynecologic, or other laparoscopic surgical procedures. The compatible endoscopic instruments and accessories for use with the surgical system are intended for endoscopic manipulation of tissue including grasping, cutting, displacement, blunt and sharp dissection, approximation, ligation, electrocautery, and suturing.

Figure 1:
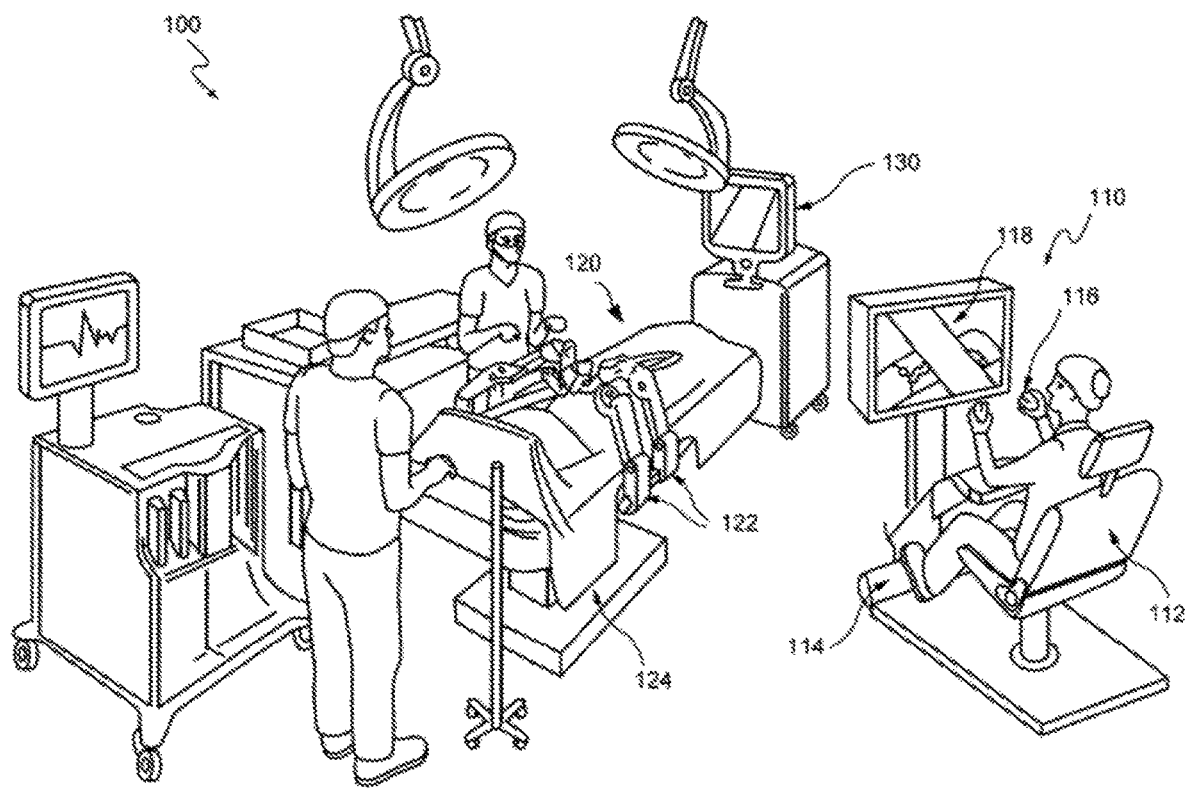
FIG. 1 is an illustration of one embodiment of an operating room environment with a surgical robotic system according to one embodiment.

FIG. 1 is a diagram illustrating an example operating room environment with a surgical robotic system 100 that may use one or more templates for automation. The surgical robotic system 100 includes a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. Additional, different, or fewer components may be provided, such as combining the control tower 130 with the console 110 or surgical robot 120. The robotic arms 122 are shown as table-mounted, but in other configurations, the robotic arms 122 may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may comprise a seat 112, pedals 114, one or more handheld user interface devices (UIDs) 116, and an open display 118 configured to display, for example, a view of the surgical site inside a patient and graphic user interface for selecting, programming, and using task templates. As shown in the exemplary user console 110, a surgeon sitting in the seat 112 and viewing the open display 118 may manipulate the pedals 114 and/or handheld user interface devices 116 to remotely and directly control the robotic arms 122 and/or surgical instruments mounted to the distal ends of the arms 122. The surgeon sitting in the seat 112 may view and interact with the display 118 for using task templates for automation of operation of the robotic arms 122 and/or surgical instruments in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, to control selection and programming of a task template, and/or to supervise automatic operation following a task template while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Some surgical tasks, such as retracting, suturing, or other tissue manipulation, may instead be performed by one or more robotic arms 122 (e.g., third or fourth arms) according to a task template. Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to a corresponding sleeve. The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore in direct teleoperation, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

Other arrangements for surgical robot systems may be used. One or more robotic arms 122 are controlled through a processor, whether a processor of the robotic arms 122, control tower 130, or console 110. This processor-based control allows for use of a task template to automate motion and/or tissue manipulation by the robotic arm 122 or arms 122.

Figure 2:
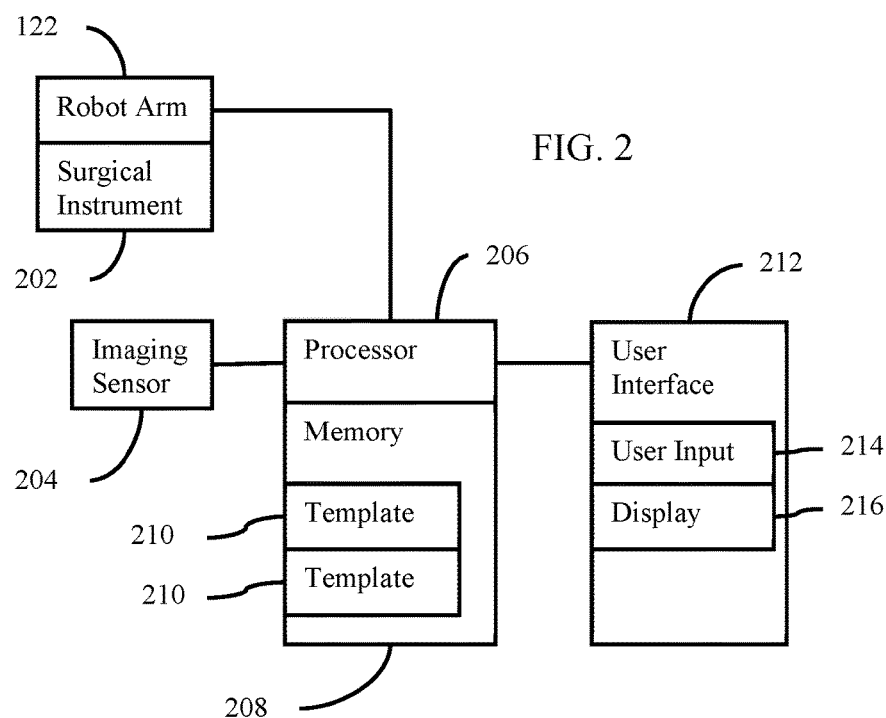
FIG. 2 is a block diagram of one embodiment of a surgical robot system using task templates for automation.

FIG. 2 shows a block diagram of one embodiment of a surgical robot system controlled, at least in part, using one or more task templates 210. The templates 210 provide for one or more surgical tasks to be automated, allowing for surgeon rest, change in focus, and/or reduction in physical input. The surgical robot system implements the method of FIG. 5, the communication flow of FIG. 6, or other methods and/or communications.

The surgical robot system includes one or more robot arms 122 with corresponding surgical instruments 202 connected with the robot arms 122, an imaging sensor 204, a processor 206, a memory 208, and a user interface 212. Additional, different, or fewer components may be provided. For example, the imaging sensor 204 is not provided. As another example, the user interface 212 is not provided where the template 210 may be used with default values.

The imaging sensor 204 is one or more cameras. X-ray, ultrasound, magnetic resonance, or other imaging systems for imaging a patient may be used. The imaging sensor 204 images an exterior or exposed part of the patient and/or interior of the patient. The imaging sensor 204 may be positioned to image the patient and the surgical instruments 202 and/or robot arms 122.

The processor 206 uses image data from the imaging sensor 204 as visual feedback to the surgeon. Alternatively, the image data is used to control one or more of the robot arms 122 and/or surgical instruments 202 during automation, such as using image data to determine the location of tissue to be manipulated. Based on calibration, the surgical instrument 202 may be placed at the tissue to be manipulated based on the image data.

The robotic arms 122 each include one or more links and joints. The joints may be pitch or roll joints. A tool drive (e.g., end effector) and cannula for receiving and guiding a surgical tool may be provided on each of the robotic arms 122. Different combinations of links and joints may define or form different parts of the robotic arms 122, such as different parts having different degrees of movement (e.g., translation and/or rotation). Any now known or later develop robotic arm 122 with motors, sensors, links, joints, controllers, and/or other structure may be used.

One or more robotic arms are provided. For example, three or four robotic arms 122 are provided. The robotic arms 122 mount to a table, such as a base of an operating table. Alternatively, cart, floor, ceiling, or other mounts may be used. The robotic arms 122 include a cable or wireless transceiver for communication with the processor 206 or an intermediary (e.g., control tower 130).

The robotic surgical instruments 202 are one or more graspers, retractors, scalpels, endoscopes, staplers, scissors, or other surgical device for manipulating tissue of the patient. The tissue manipulation may be direct, such as cutting or grasping. The tissue manipulation may be indirect, such as an endoscope pressing or contacting tissue as guided to image or view an interior portion of the patient. Different or the same type of instruments 202 may be mounted to different ones of the robot arms 122. For example, two robot arms 122 may have graspers, a third robot arm 122 may have a scalpel, and a fourth robot arm 122 may have an endoscope.

The robotic surgical instruments 202 connect to the distal ends of the robot arms 122 but may connect at other locations. The connection is to an end effectuator so that the tool may be operated, such as closing a grasper or scissors.

The processor 206, memory 208, and user interface 212 are part of a computer or workstation, such as being part of the surgeon or user console 110. Alternatively, the processor 206, memory 208, and user interface 212 are part of the control tower 130. In other embodiments, the processor 206, memory 208, and/or user interface 212 are part of different control systems, such as the processor 206 and memory 208 being part of the control tower 130 while the user interface 212 is part of the user console 110. In yet other embodiments, any one of the processor 206, memory 208, and/or user interface 212 may be distributed between different systems, such as the processor 206 and memory 208 each including processors and memories of more than one computer (e.g., the user console 110, the control tower 130, the robot arms 122, a server, and/or a remote workstation).

Figure 3:
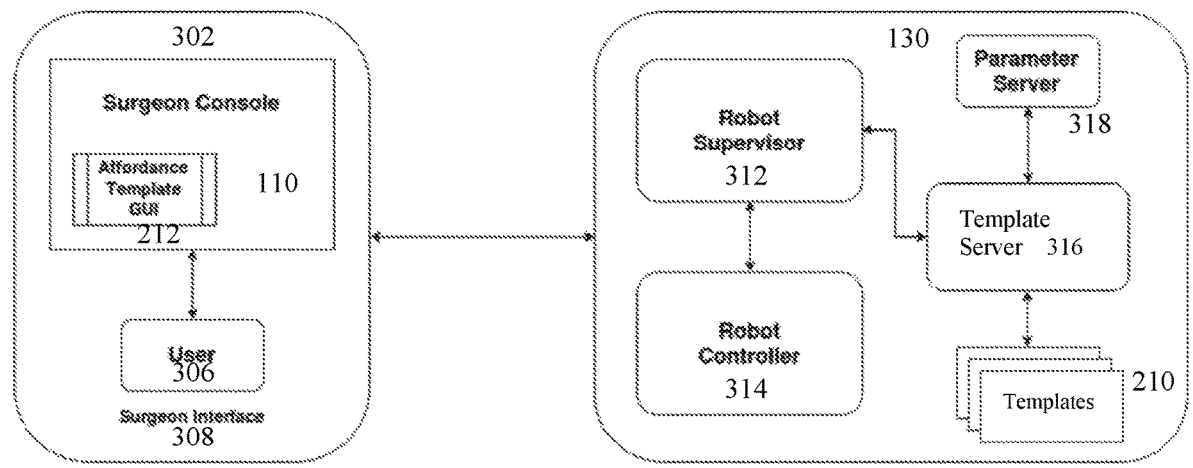
FIG. 3 is a block diagram of an embodiment of a control arrangement for use of surgical task templates in surgical robot system operation.

The processor 206, memory 208, and user interface 212 form a control architecture for use of templates to automate one or more tasks of one or more robot arms 122 as part of a surgery. FIG. 3 shows an example control architecture or arrangement. A template system 302 includes the surgeon console 110 with a graphics user interface 212 for task templates, such as surgical task templates, as part of the surgeon interface 308 for the surgical robotics system. The user 306 uses the surgeon interface 308 to control the robot arms 122 directly and/or through use of one or more templates 210 of the template graphics user interface 212. The control tower 130 includes, for each robotic arm 122, a robot controller 314 receiving control instructions from a robot supervisor 312. The robot supervisor 312 uses output of waypoints and/or other information from the surgical task template server or process 316 running the surgical task template application, which uses parameters from the parameter server or process 318 and a template from the surgical task templates 210 in a library. The parameters from the parameter processor or server 318 and the template from the surgical task templates 210 may be selected and input as part of pre-planning or during surgery. Other control architectures may be used.

The memory 208 is a random-access memory, system memory, cache memory, hard drive, optical media, magnetic media, flash drive, buffer, database, combinations thereof, or other now known or later developed memory device for storing the templates 210 and settings of parameters of the templates. The memory 208 stores one or more templates 210, such as a library of available templates 210 or templates 210 identified through pre-planning as useful in the current surgery. Other types of data may be stored, such as image data from the imaging sensor 204, control instructions of the robot controller 314 and/or robot supervisor 312, robot arm position information, sensor data (e.g., strain gauge or other values from robot joints), currently equipped surgical instrument identification, logging of user input, logging of robot arm 122 and/or surgical instrument 202 operation, and/or graphical user interface information. A pre-operative plan may be stored for access by the user during surgery. Medical imaging, such as computed tomography, magnetic resonance, ultrasound, or x-ray, data may be stored for generating images in guidance of the MIS.

The memory 208 is configured by the processor 206 and/or formatting to store one or more task templates 210. A library of different task templates 210 corresponding to different surgical tasks may be stored.

Each task template 210 is directed to a different task. The tasks are routine or repeatable steps, such as tasks that may be repeated for different patients, different times in a surgery, and/or for different types of surgery. Some example tasks using automation of multiple steps by one or more robotic arms 122 include suturing, knot tying, running a colon or intestine, retraction, tissue tensioning, and endoscope guidance. Task templates 210 may be provided for any surgical task (e.g., any action or step used in surgery, such as MIS surgery, and/or any tissue manipulation act).

For example, the task template 210 for running a colon defines steps to be performed by the robotic arm 202 and surgical instrument 202 during gastric bypass procedures. The intestine is "run" to measure how long of a bypass tube needs to be cut. Many surgeons visually estimate by jogging (e.g., grasping along the colon in a laddered fashion to measure in increments) the colon between two end effectors. The task template for jogging the colon automates the process, improving the accuracy of the lengths being measured and providing less cognitive fatigue on the surgeon.

Another example task template is for knot tying. The surgeon sets the robotic arms 122 at some initial position with thread in a grasper. The task template then defines the movements of the robotic arm(s) 122 and surgical instrument(s) 202 to tie a knot. Other suturing operations may be provided by other task templates. One task template may include multiple different tasks.

Yet another example task for a task template is retraction. The surgeon can place tissue in the tool of a robot, then set a specified distance to maintain for retraction. The robotic arm 122 automatically maintains the distance, moving to account for any changes due to patient movement and/or actions by the surgeon using others of the robotic arms 122 in direct control. The automation allows use of a third or fourth robotic arm 122 based on the task template while directly controlling other robotic arms in teleoperation, effectively having three or more arms moving for a task under one surgeon.

In another example, the task template is for the task of tissue tensioning for cutting. In direct control, the surgeon grasps tissue with graspers on two robotic arms 122. The tension to maintain is defined in the task template. The task template is activated, causing the two robotic arms 122 to maintain the tissue between them at the set level. The robotic arms 122 move to maintain the tension. The surgeon may then directly control another robotic arm 122 to cut. Alternatively, the task template 210 or a separate task template 210 is used to automate the cutting.

The library of task templates 210 in the memory 208 includes any number of task templates 210 for any number of surgical tasks. The templates 210 may be used separately, singly, or independently of each other or used in combination. The availability of task templates for or during a given surgery may be restricted by the type of surgery, patient characteristics, and/or pre-planning. Alternatively, the full library is available to the surgeon at any given time. The task templates 210 in the library may be limited for policy reasons, based on guidelines, based on standards, and/or for other reasons. For example, the availability of task templates 210 restricts what may be performed automatically, such as avoiding automation of any cutting or determining where to cut.

The task templates 210 define operation of one or more of the robotic arms 122 and/or surgical instruments 202 in the surgical task. The task templates 210 include instructions to control one or more robotic arms 122 through one or more motions and corresponding waypoints, including repositioning a surgical instrument 202 and/or operating the surgical instrument 202 (e.g., closing and/or opening scissors or graspers, or cutting with a scalpel). The task templates 210 include operating the robot arms 122 and instrument 202 in a way that manipulates tissue. Each of the task templates 210 includes a sequence of steps or acts to achieve a surgical task for automated performance of tissue manipulation by the robotic arms 122 and instruments 202. The steps or acts are a motion trajectory for one or more of the robotic surgical instruments 202. The trajectory or pathing between tissue manipulations may be defined, such as to avoid blood vessels, neural paths, or other tissue.

The template architecture is a software-based object. The templates 210 are the skeleton of the motion to be automated. In the case of "running" intestines, the skeleton defines the main axis of motion based off of the initial pose (i.e., position and/or orientation) of each instrument 202. The skeleton uses the Euclidean distance between end effectors and the desired length to run to define a number of iterations in the ladder or sequential running. The motion to be automated may be defined in any of various ways, such as vector, trajectory, and/or waypoint parameterization.

The software object may be defined in various ways. For example, the object is a generalized parametric motion trajectory algorithm. As another example, the object is a generalized artifact created from machine learning. The machine learning learns to imitate the motion from many examples collected as training data. Many samples of logging data showing the task being performed by the robot arms 122 and instruments 202 under direct teleoperation are available. The logging data provides for motion, robot joint positions, and/or other parameterization of the robotic motion during the task. The machine learning generalizes the training data into the template. Various machine learning approaches may be used, such as imitation, task-based, or instance learning. In one embodiment, reinforcement learning, such as deep reinforcement learning with a neural network, is used. The machine learning trains a policy to determine next acts in a sequence of acts to achieve the end result (task). The reinforcement learning trains with a reward to encourage selection of acts most likely to achieve the end result.

In one embodiment, the task templates 210 are surgical task templates (e.g., affordance templates directed to surgical tasks). The surgical task templates provide for additional collaboration. A surgical task template describes a place or object in the world that affords an action by a particular agent. In the surgical context, the surgical task template includes models of the tissue and the surgical robot. The surgical task template is a construct that allows for a human to help inform a robot or autonomous agent of the types of actions or behaviors that can be applied to a specific object. The human may provide the motivation of the tasks, and the template allows for a high-level way to get the robot to complete a task without direct teleoperation of the joints. In a surgical context, the surgical task templates are constructs that a user will use to setup the system. Specific surgical actions such as retract or run tissue, suture, cut, etc. are employed with various templates that can range from a generic tissue object (a flat "sheet" of biological tissue) to more specialized shapes such as the stomach or liver. The templates may also be applied to other surgical tools, such as needles for a needle driver. The template of a surgical needle has the actions OF suture in a line or tie a knot. Surgical task templates including surgical robot and/or tool models including physical and kinematic features and patient general and/or specific models, such as including health record, anatomy and/or surgical site information. The surgical task template includes models of the tissue and the actions the surgical robot can enact on the objects in the robot's environment.

The tissue model may be a generalized model of an organ, group of organs, or entire body. The tissue model may be specific to the patient, such as a model created from or fit to a medical scan of the patient. The surgical task templates model actions that can be performed on objects in a robot's environment. Tissue models are models capturing physical structure. Tissue models of different organs, such as the liver or bowels, are provided. Each different organ or tissue model has a set of possible tasks grouped in one or more templates for different surgical actions. For example, the retract action on a liver is different than the retract motion on the bowels. The bowels would have a "run" action, but that's not an option for the liver. Different surgical task templates with the corresponding surgical actions are provided for the different organs even with a same task. The surgical task template allows for a surgeon to move from "joint" level control to task level sequencing and planning for the robot arm 122 and instrument 202 to interact with the modeled tissue. The surgical task template uses the object modeling in pre-planning or defining the motions for automation, shifting the work of the surgeon from direct one-to-one control of the robotic arms 122 to task-based sequencing, planning, and supervising based on modeled interaction.

The object or tissue model is used to define the motion and/or to represent interaction of pre-defined motion with tissue. The object model may not be used during active control, such as not using the object model to change the motion while the motion occurs. Alternatively, the object model is aligned with the tissue, such as using the imaging sensor 204 to align. The motion of the robotic arm 122 may vary based on the alignment and planned interaction of the motion with the object model.

In one embodiment, the task templates are pre-defined. By selecting the task template, the automated actions of the robotic arms 122 and the surgical instrument 202 are set. In other embodiments, the task templates include one or more parameters that may have default values that can be set or changed in pre-planning and/or during surgery. The values of the parameters control one or more movements, steps, or operations of the task template 210. The task being implemented by the task template is controlled based on one or more values of parameters where the values may be altered or changed.

For example, the parameters are for a force level. The magnitude of the force, such as for pulling, pressing, or moving of tissue, is limited using the value. The robotic arms 122 and surgical instruments 202 are limited to (e.g., not exceed, or not to go below) or used to apply the set force level within tolerance. Other examples include the distance of movement, trajectory or pathing of the surgical instrument 202 during movement, waypoint location, an order of motions, operations, speed, or which tasks or steps to achieve the task. Another example is the timing relative to acts or motion of supervisory stops or stop locations. For example, the automation is made to stop at user selected positions or times within a sequence of motion. The user may verify proper performance without being rushed when a stop occurs. The automation would then continue after input by the user. The locations of these stops or other supervisory processes are selected by the surgeon.

In the example of running the intestines, the programmable parameters may be the axis of motion (i.e., direction along which the intestines are run), a distance (e.g., Euclidean distance between surgical instruments 202 for each iteration in running along the intestines), a total distance to run, and/or a number of iterations for running. A trajectory planner of the task template 210 plans a desired set of trajectories for each arm 122 to work in tandem for the lower grasper to reach upwards some set distance, grasp, then have the upper grasper release for the lower grasper to pull downwards, and repeat until the desired length is run.

The user interface 212 is a graphics user interface for interaction of the surgeon with the surgical robot system, such as with the processor 206 for controlling the robotic arms 122. The user interface 212 includes a user input 214 and a display 216. The user input 214 and/or the display 216 are provided at the user console 110 and/or control tower 130 but may be at other locations.

The user input 214 is a button, a keyboard, a rocker, a joy stick, a trackball, a voice recognition circuit, a mouse, a touch pad, a touch screen, sliders, switches, UID 116, foot pedal 114, combinations thereof, or any other input device for inputting to the surgical robot. The display 216 is a monitor, liquid crystal display (LCD), projector, plasma display, CRT, printer, or other now known or later developed device for outputting visual information. In an alternative embodiment, the display 216 is a head mounted display. The user input may be a sensor or sensors for detecting eye movement and/or blinking. In yet other embodiments, the user input 214 is a microphone for voice-based input. A speaker for output of audio information may be provided instead of or in addition to the display 216.

The user interface 212 is configured by an operating system and/or the processor 206 to provide output to the surgeon and/or receive input from the surgeon. The user interface 212 is used to select one or more of the task templates 210. The user interface 212 is used to input a setting or settings for one or more parameters of the selected task template 210. For example, the distance of movement, a force level for one of the surgical instruments in manipulation of the tissue, a location in the sequence for a stop point for user verification, waypoint, speed, and/or an order of the tasks in the sequence are input. The stop point may be a time and/or pose (e.g., location and orientation) of the tools or arms. In other embodiments, the input may be by operation of the robot arms 122 and/or surgical instruments 202. A distance and/or axis of motion may be based off of an initial pose of end effectors (i.e., robot arms 122 and surgical instruments 202). The surgeon places, operates, and/or moves the surgical instruments 202 as an input to select and/or set one or more parameters or templates. Image data from the image sensor 202 may be used for the selection and/or setting.

In one embodiment, the selection of a template 210 and/or setting of a parameter is provided as a menu selection. A list of options is presented to the user. Input boxes, drop down lists, windows, tabs, selection buttons, and/or other user interface objects may be used for the selection and/or setting.

Figure 4:
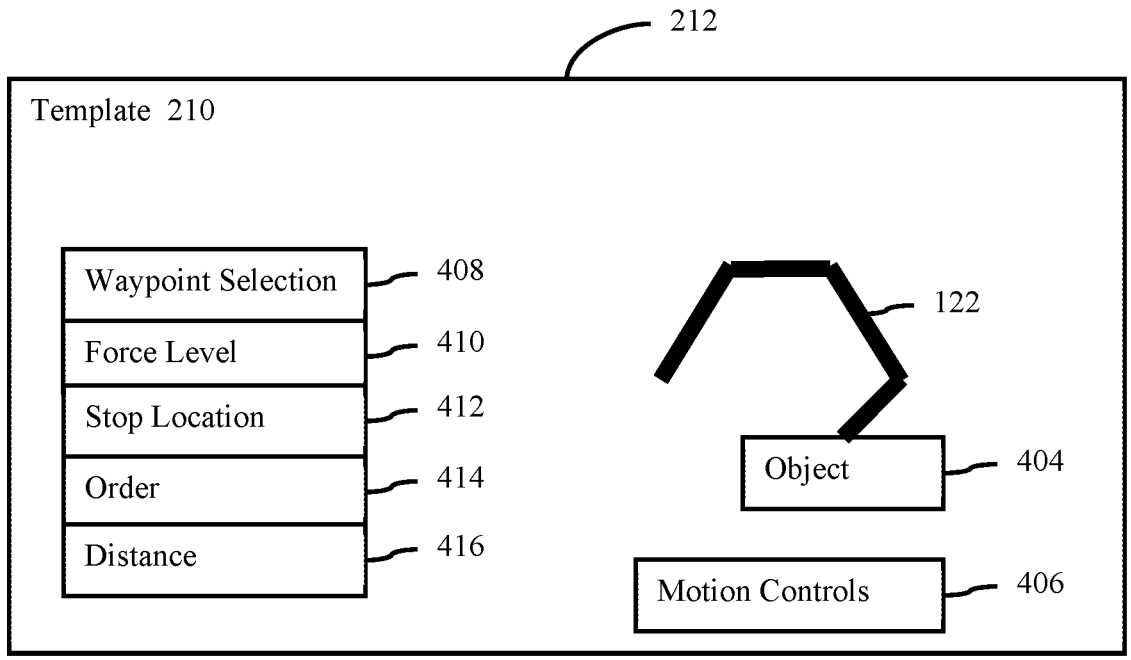
FIG. 4 illustrates an example graphic user interface for setting values for an surgical task template.

For a surgical task template, the setting of a parameter may include modeling the interaction between the robotic system and the tissue model. FIG. 4 shows an example. A representation over time of the robot 122 performing the tasks of the selected task template is provided. The object 404 with which the robot is to interact is modeled in the representation. Using motion controls 406, such as controlling the location (e.g., waypoints), speed, playback, or other motion, the sequence of steps or motion may be simulated. Different waypoints to achieve the task may be selected in the waypoint selection 408. The surgeon uses the motion controls 406 to simulate moving to the waypoint, the location of the waypoint (i.e., surgical instrument 202 relative to the tissue or object 404), and/or to set the motion to get to the waypoint. By cycling through the waypoints for the selected template 201, the surgeon sets programmable parameters of the task. Inputs are provided for setting any number of input parameters, such as the force level 410, stop locations 412 in the process, order 414 of steps, distance 416, and/or other parameters. One or more parameters (e.g., distance) may be set based on use of the motion controls 406 and/or clicking and dragging the object 404, surgical instrument 202, and/or arm 122 in the representation.

The display of the representation is used to program and plan automated performance of the task prior to actual performance, allowing the surgeon to deal with patient or situation specific differences. Once programmed, a preview of the calculated paths may be visualized on the graphics user interface 212 for the surgeon to preview and accept or to make alterations. During actual automation, the trajectory will just start once triggered but can be interrupted by the surgeon to take direct control over at any time.

The selection and setting may occur as part of pre-planning. Before the patient is prepared for surgery and/or placed on the surgical bed, the template or templates 210 are selected and any settings are changed or confirmed.

In other embodiments, the selection of the template 210 and/or setting of one or more parameters of the selected template 210 occur during the surgery. After the patient is placed on the surgical bed and/or after puncture or cutting of the patient, the surgeon uses the user interface 212 to select a template 210 and/or set one or more parameters of a selected template 210. For example, the surgeon reaches a point in the surgery where a knot is to be tied. To have a physical and/or mental break, the surgeon pauses or stops direct control of the robotic arms 122. The surgeon activates the user interface 212 to select a template 210 from the library. The knot tying template 210 is selected from a list. The affordance or other task template is then used to set one or more parameters, such as a type of knot or distance between entry and exit points in the tissue for tying the knot. Interaction with the model of the tissue and the surgical robot may be modeled for setting the parameter. Once programmed, the user may activate the automation and/or may place the surgical instruments 202 as appropriate to start the automation under direct control to then activate the automation embodied by the template 210 as programmed. For example, an activation button is presented on the user interface 212 once the user verifies positioning of the instrument(s) 202 against the tissue to be manipulated.

In another embodiment, the imaging sensor 204 is used by the processor 206 to determine that a given template may be appropriate. Once the instruments 202 are in a position appropriate for the template, the surgeon is prompted that a template to start and complete a task from the current placement is available. The user the selects and programs the template 210, allowing for display of an activation based on the positioning of the instruments 202 against the tissue.

Once activated, the surgeon supervises the automated performance of the task. The surgeon may stop the automation at any time, such as using a "stop" button on the user interface 212 or re-engaging teleoperation to take direct control. This interruption from the surgeon stops the sequence of motions in the template 210. In some embodiments, the automation may automatically stop at one or more locations or times in the process or sequence of movements. The automation then continues once the surgeon confirms or verifies proper performance.

The processor 206 is a computer that drives the robotic arms 122 and/or surgical instruments 202. The processor 206 is a general processor, central processing unit, control processor, graphics processor, graphics processing unit, digital signal processor, application specific integrated circuit, field programmable gate array, digital circuit, analog circuit, artificial intelligence processor, combinations thereof, or other now known or later developed device for controlling the surgical robot. The processor 206 is a single device or multiple devices operating in serial, parallel, or separately. For example, the processor 206 is one computer on the user console 130 for the user interface 212 and another computer on the control tower 130 for controlling or driving the robotic arms 122 and instruments 202 based on the template 210. The processor 206 may be a main processor of a computer, such as a laptop or desktop computer, or may be a processor for handling some tasks in a larger system. Based on hardware, software, firmware, or combinations thereof, the processor 206 is configured to implement instructions or perform acts.

The processor 206 is configured to implement the user interface 212. Using an operating system, the processor 206 provides for selection of a template, programming of a setting of the template, and/or switching between direct and automated control of the robotic arms 122.

The processor 206 is configured to drive or control the robotic arms 122 and instruments 202 based on teleoperation by the surgeon. Inputs from the surgeon are translated into movement or operation of the robotic arms 122 and instruments 202. This direct control allows the surgeon to perform the surgery without automation of surgical tasks. The movement of the arms 122 in the form of which joint is activated and by how much may be automated to provide for the desired positioning of the instruments 202 under direct control by the physician. This direct control avoids the surgeon from having to control each joint of the robotic arms 122 separately. The surgical task being performed (e.g., how the tissue is manipulated) is not automated.

The processor 206 is configured to automatically drive or control the robotic arms 122 and/or instruments 202. Upon activation of automation, the selected task template 210 is followed. The processor 206 moves the arms 122 and instruments 202 to perform the surgical task and manipulate tissue without direct control from the surgeon. One or more arms 122 may be directly controlled while one or more other arms 122 are automatically controlled based on the template or templates. All arms 122 may be automatically controlled based on the template 210. The settings of the parameters of the template 210 are used in the automatic control.

The processor 206 is configured to stop automation or stop movement based on the template 210. One or more robotic arms 122 are controlled to cease movement after one step or task is performed and before another of the steps or tasks of the selected task template are performed. The arms 122 and instruments 202 are stopped at a location (i.e., time or waypoint) in the sequence. The automation continues once the surgeon verifies that automation should continue. The processor 206 is configured to stop the automation at any time upon receipt of an interruption, such as from the surgeon or from a collusion sensor.

The memory 208 or another memory is a non-transitory computer readable storage medium storing data representing instructions executable by the programmed processor 206 for robotic surgery (e.g., teleoperation and/or automatic operation) by a surgical robot. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Instructions are provided for any of the acts discussed herein. In one embodiment, the instructions are for setting values for parameters of a surgical task template for surgery by the surgical robot. The instructions are also for automatically operating the surgical robot in surgery according to the surgical task template with the set values. Instructions for various steps or acts to automatically perform a surgical task are provided.

Figure 5:
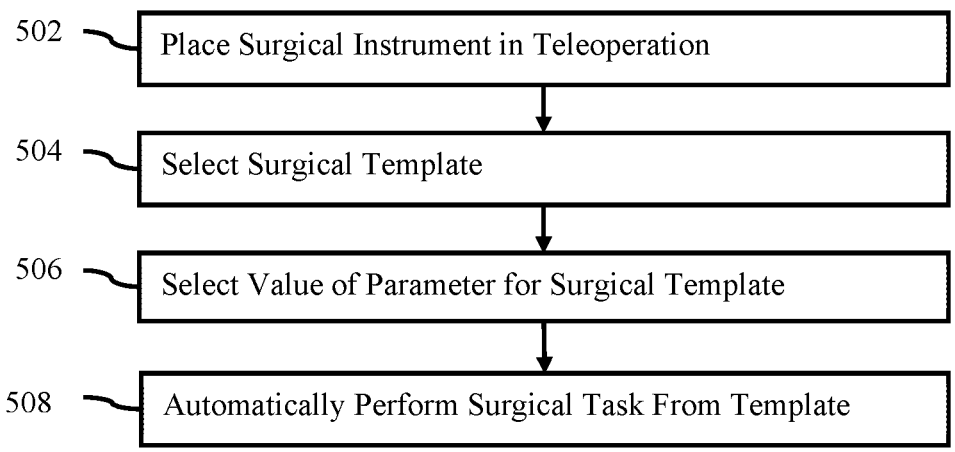
FIG. 5 is a flow chart diagram of one embodiment of a method for surgery by a surgical robot system.
Figure 6:
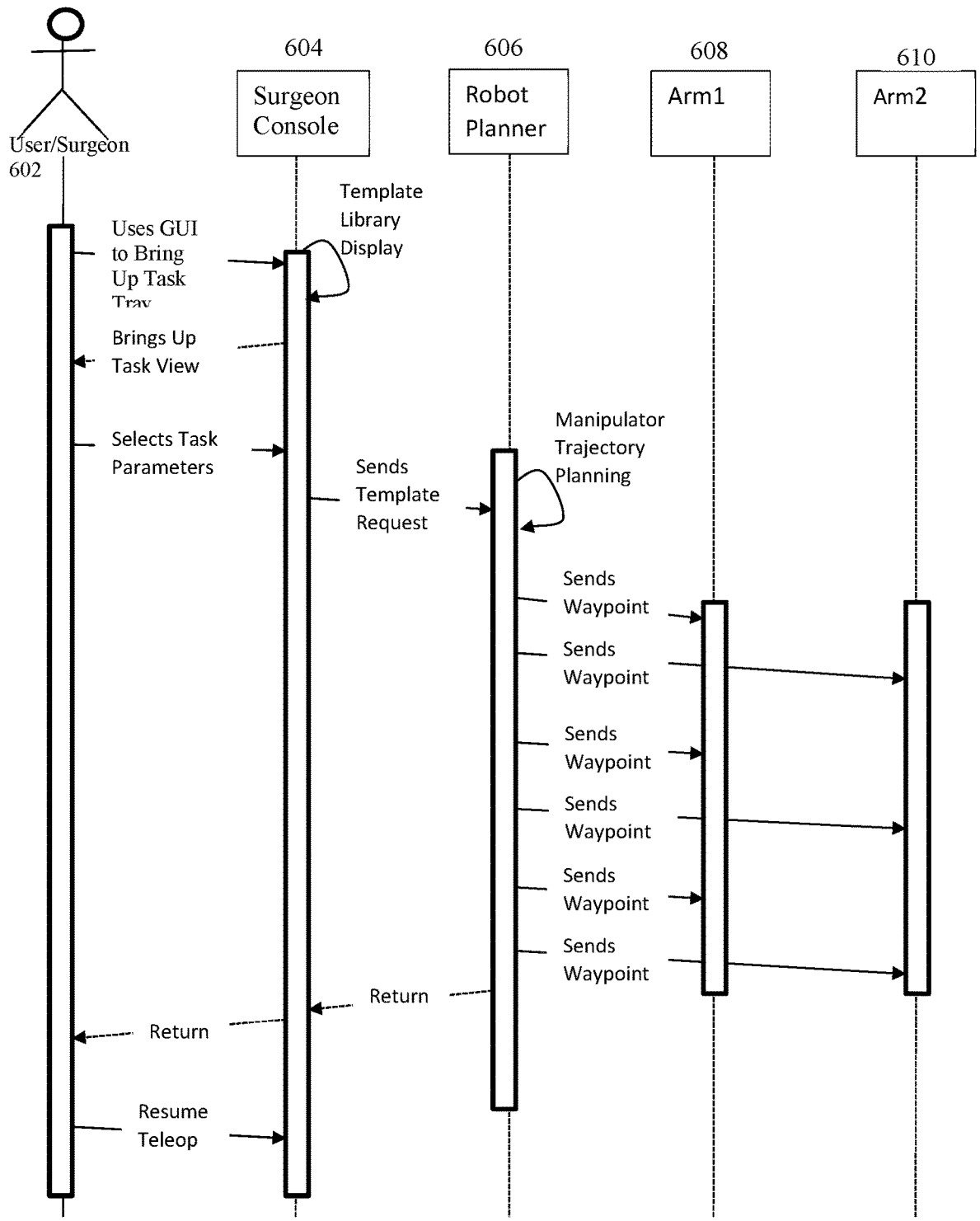
FIG. 6 illustrates a communication flow for use of a task template in control of a surgical robot.

FIG. 5 show one embodiment of a method for surgery by a surgical robot. One or more task templates are used to automate performance of a surgical task by the surgical robot under supervision of the surgeon. FIG. 6 shows communications that occur as part of this embodiment of the method. Other communications may be used.

The method is implemented by the surgical robot system of FIG. 1, the system of FIG. 2, the control architecture of FIG. 3, or another system or surgical robot. Additional, different, or fewer acts may be provided. For example, act 506 is not provided. As another example, acts for pre-operative planning and/or acts for directly controlled teleoperation are provided. The acts are performed in the order shown or other orders. For example, acts 504 and/or 506 are performed prior to act 502.

In act 502, the user places, in teleoperation, one or more surgical instruments relative to tissue or another surgical site (e.g., implant or other location within the patient) using a robot arm or arms in surgery of a patient. Direct control is used to operate on the patient. In preparation for automation, the surgeon places the instruments in contact with tissue or in a position with an expected or known spatial relationship to the tissue or the other surgical site of the patient. The contact may be resting against or grasping.

The surgeon recognizes the tissue in a current situation, determines that a template may be used to perform a surgical task, and places the surgical instruments as appropriate for the automation. For example, the surgeon is performing active teleoperation on a patient. The surgeon is to run the intestines of the patient to determine the length of intestine that may be removed. The surgeon places the graspers of two robotic arms at a desired relative orientation and distance apart. The robotic arms are set up with an initial grasp of the intestines. Rather than manually running, the surgeon is to select a template for running after positioning the graspers.

Alternatively, the template selection and/or programming is started. Based on the selection and/or programming, the user then places the instruments in preparation for the automation. The surgeon may then trigger supervised autonomous movements of the robotic arms and instruments.

In another alternative, the user or surgeon does not use teleoperation. Instead, different templates in the robot's environment or workspace are selected. A sequence of tasks for procedures are defined using the selected templates. The templates are used for all position and trajectories in the surgical procedure or at least for the beginning of the surgical procedure. Teleoperation is not used or is used later in the surgery.

In act 504, the user selects a surgical template from a menu. The menu is activated, changing from the teleoperation to a graphics interface for the menu. The change in operation modes results in holding the robot arm and surgical instrument in place. The surgery moves from active teleoperation to disengaged operation with a graphics user interface tool bar and/or panel.

The user selects the desired surgical template, such as a surgical task template, from a library of templates. The different templates are for different tasks, so the user selects the template for the desired task. The templates available for selection on the menu may be restricted based on a position of the surgical instruments relative to tissue of the patient, each other, type of surgery, and/or pre-planning. For example, the pose of the surgical robot is used to limit the library and/or to highlight or propose a likely task to be selected. Alternatively, the entire library is available.

The user selects the template by selecting the task. The menu is used to select the template in any manner.

Referring to FIG. 6, the surgeon 602 uses the graphics user interface to load or bring-up a task tray. The surgeon console 604 displays the template library, such as a list of tasks. Upon selection of the task and corresponding task template, the task view is brought up for the surgeon 602.

In act 506 of FIG. 5, the user selects a value of a parameter of the selected surgical template. Values that change over time for one parameter and/or values for different parameters of the same template may be selected. The parameter is set for automated operation of the surgical robot using the template.

In alternative embodiments, default values are provided. The user selects the default values, such as not changing the values. The defaults may be values for different patients. Alternatively, the values for a given patient are established as defaults during preoperative planning of the surgery for the patient. The user confirms during selection of the values that the defaults remain appropriate or changes the defaults.

The template may include options for settings. A range of values, different preset values, or constraints on values may be used in the selection.

The selected template may indicate which values may be changed. Any of various parameters may be set, such as selecting a value for a force level, a waypoint location, a stop point in movement of the surgical instrument or robot arm for user verification, or an order of operations of the robot arm. Some parameters may not be changed. Alternatively, any setting of any parameter in the parameterization of the movement or operation of the surgical robot may be set.

In one embodiment, the user interacts with the selected template, such as interacting with the surgical task template. Models of the surgical robot and the object to be operated on (e.g., patient or tissue) are displayed. The user uses the representation to select values, such as guiding the interaction or tissue manipulation in a simulation (i.e., representation of the robot arm and surgical instrument performing the surgical task). The desired values are selected using interaction with the simulation, such as trying different values to visualize the effect and/or controlling the simulation to provide the value or values.

For example, a running colon template is selected. The template defines the tissue model and defines or calls a robot model. The template defines the operations and corresponding settings used in running a colon. The tissue model is of a curved or folded tubular structure. Two robotic arms and grasping tools are modeled to interact with the tissue model. The user may select different operations to set, such as running operations and releasing operations. The user sets a number of times to grasp and run along the colon (tissue model) given an initial distance apart of the graspers in a starting position. The user may set the initial distance apart and/or a length of each run (distance between graspers before one grasper releases and moves to a next grasping location). The user may set an arch or path for a grasper to travel when not holding the tissue model and/or when running along the tissue model. As part of setting and/or to provide information, the interaction of the robot model with the tissue model is displayed. The user may change any settings upon or during viewing of the simulation of the interaction of the models in the template. The user may set a length, circumference, diameter, elasticity, and/or other characteristics of the tissue model. Characteristics of the robot model may be set. Default values may be used for one or more characteristics.

In another example, a dissection template for Gastric Neoplasia is selected. The tools modeled for this task are a hook, scissors, and/or grasper on two or three robotic arms. The tissue model is of the gastric system with a cancer or other lesion. Various operations for holding and/or grasping may be defined, such as grasping the lesion or grasping tissue next to the lesion. Various operations for cutting the lesion or around the lesion may be defined. Various operations for hooking, dragging, or applying pressure may be defined. Various operations for pathing or trajectory of movement may be defined. The user sets the range of motion, pressure, placement relative to the lesion, and interaction of different operations for dissection. The size, tissue characteristics, shape, and/or other characteristics of the lesion and/or tissue around the lesion may be set. Based on the interactive display simulating interaction between the tools and tissue model, the user sets the values of parameters of the template (i.e., selected operations provided in the template). In yet other examples, the operations, models, and/or parameters that may be set are provided for robotic suturing and/or knot tying.

In FIG. 6, the surgeon 602 selects the tasks of the surgical template and parameters for the tasks from the task tray. The values for the tasks are provided to the surgeon console 604, which sends a template request for automated control to the robot planner 606 (e.g., controller of the surgical robot).

In act 508 of FIG. 5, the surgical robot automatically performs a surgical task. One or more robot arms and/or surgical instruments follow the selected surgical template based on the value or values of the parameter or parameters. The template is used to control the surgical robot to implement the surgical task. The robot arm or arms and instrument or instruments are moved automatically.

The user does not directly control the movement during the movement. The user may control by previous template selection and/or value selection, but the template is used without user control (i.e., no direct control) during the performance of the sequence of movements. The user may control one or more arms and/or instruments, but one or more other arms and/or instruments are controlled automatically by the selected template as programmed (i.e., based on the selected values).

In FIG. 6, the robot planner 606 uses the template to plan the trajectory of one or more arms. In the example of FIG. 6, the trajectory of two arms 608 and 610 are planned. The surgical instruments on those arms 608, 610 are moved to various waypoints in sequence. The robot planner 606 sends the waypoints or instructions for reaching the waypoints to move the arms 608, 610 in the desired sequence. The motion is controlled based on the template. This automated control executes the surgical task. Upon completion of the task, the process returns for further direct control (i.e., teleoperation) by the user 602 or for further template selection and programming.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A surgical robotic system comprising:
   one or more robotic arms;
   one or more surgical tools each coupled to a distal end of the respective one or more robotic arms;
   a memory configured to store a plurality of task templates, each of the task templates including a sequence of steps interacting with tissue of a patient, the steps being for automated performance of a surgical task by the surgical tools, and each of the task templates including one or more parameters controlling one or more of the steps of the respective task template;
   a user interface configured for user selection of one of the task templates and settings for the one or more parameters for the selected task template, the one or more parameters for the selected task template comprising: a trajectory of arm and/or tool movement, a force level for tissue manipulation, a stop point for user verification, and/or an order of the steps in the sequence; and
   a processor configured to automatically drive the one or more robotic arms and the one or more robotic surgical tools based on the selected task template and the settings.

2. The surgical robotic system of claim 1 wherein the task templates include suturing, running a colon, retraction, tissue tensioning, and endoscope guidance templates.

3. The surgical robotic system of claim 1 wherein the one or more parameters for the selected task template is the force level.

4. The surgical robotic system of claim 3 wherein the force level is a magnitude of force applied by the robotic arm or arms to the tissue.

5. The surgical robotic system of claim 1 wherein the one or more parameters for the selected task template is the trajectory.

6. The surgical robotic system of claim 1 wherein the one or more parameters for the selected task template is the stop point, the processor configured to drive the one or more robotic arms to cease movement after one of the steps and before another of the steps of the selected task template at a location in the sequence and to perform the other of the steps automatically in response to user input of activation.

7. The surgical robotic system of claim 1 wherein the one or more parameters for the selected task template is the order of the steps in the sequence.

8. The surgical robotic system of claim 1 wherein the user interface is configured to display a representation over time of the robot performing the steps of the selected task template, and wherein the user interface is configured to receive the input of the setting in response to display of the representation.

9. The surgical robotic system of claim 1 wherein the task templates comprise surgical task templates.

10. The surgical robotic system of claim 1 wherein the sequence of the steps comprises the trajectory for one or more of the one or more robotic surgical instruments.

11. The surgical robotic system of claim 1 wherein the user interface is configured to display an activation of the selected task template once the user positions at least one of the robotic surgical instruments against the tissue.

12. The surgical robotic system of claim 1 wherein the user interface is configured to receive an interruption from the user during performance of the sequence by the robotic arms, and wherein the processor is configured to cease the sequence in response to the receipt of the interruption.

13. A method for surgery by a surgical robot, the method comprising:
    placing, by a user in teleoperation, a surgical instrument in contact with tissue relative to a surgical site using a robot arm in surgery of a patient;
    selecting a surgical template from a menu, wherein selecting the surgical template comprises changing from the teleoperation to a graphics interface for the menu, the changing holding the robot arm and surgical instrument in place;
    selecting a value of a parameter of the selected surgical template; and
    automatically performing a surgical task by the surgical robot following the selected surgical template based on the value of the parameter, the automatic performance including movement of the robot arm and surgical instrument without the movement being controlled by the user during the movement.

14. The method of claim 13 wherein selecting the surgical template comprises selecting a surgical task template from a library of surgical task templates, the surgical task templates of the library corresponding to different surgical tasks.

15. The method of claim 14 wherein the menu restricts a list of the surgical task templates for selection based on a position of the surgical instrument relative to the surgical site of the patient.

16. The method of claim 13 wherein selecting the value comprises selecting a trajectory, a force level, a waypoint location, a stop point in movement of the surgical instrument or robot arm for user verification, or an order of operations of the robot arm, options for the values being defined by the selected surgical template.

17. The method of claim 13 wherein automatically performing comprises moving the surgical instrument and/or robot arm to a sequence of waypoints.

18. The method of claim 13 wherein selecting the value comprises interacting with the selected surgical task template and a displayed representation of the robot arm and surgical instrument performing the surgical task.

19. A non-transitory computer readable storage medium having stored therein data representing instructions executable by a programmed processor for automated robot surgery by a surgical robot, the storage medium comprising instructions for:
    setting values for parameters of a surgical task template for surgery by the surgical robot, the values set from input by a user where a list of the parameters are provided by the surgical task template in a graphics interface, wherein setting the values comprises interacting with the surgical task template and displaying a representation of the surgical robot and a surgical instrument performing the surgical task; and
    automatically operating the surgical robot in surgery according to the surgical task template with the set values.

* * * * *